(12) United States Patent
Masson et al.

(10) Patent No.: US 7,195,593 B1
(45) Date of Patent: Mar. 27, 2007

(54) LIGAMENT RETRACTOR ASSEMBLY

(75) Inventors: Marcos V. Masson, Houston, TX (US);
Mark H. Henry, Houston, TX (US)

(73) Assignee: SI-1, Ltd., Conroe, TX (US)

( * ) Notice: Subject to any disclaimer, the term of this patent is extended or adjusted under 35 U.S.C. 154(b) by 0 days.

(21) Appl. No.: 10/185,358

(22) Filed: Jun. 28, 2002

Related U.S. Application Data

(63) Continuation-in-part of application No. 10/109,099, filed on Mar. 29, 2002.

(51) Int. Cl.
*A61B 1/32* (2006.01)

(52) U.S. Cl. ...................................... 600/235; 600/210
(58) Field of Classification Search ................. 600/201, 600/210, 211, 213, 214, 226, 227, 229, 235, 600/236, 237, 238, 239, 217, 219; 606/90, 606/105
See application file for complete search history.

(56) References Cited

U.S. PATENT DOCUMENTS

| | | | | |
|---|---|---|---|---|
| 856,352 | A | * 6/1907 | Magoon | 600/238 |
| 2,695,607 | A | * 11/1954 | Hipps et al. | 600/210 |
| 3,731,673 | A | * 5/1973 | Halloran | 600/210 |
| 3,762,401 | A | * 10/1973 | Tupper | 600/217 |
| 3,916,879 | A | * 11/1975 | Cotten | 600/242 |
| 4,520,797 | A | 6/1985 | Petersen | |
| 5,074,865 | A | * 12/1991 | Fahmy | 606/54 |
| 5,307,790 | A | * 5/1994 | Byrne | 600/206 |
| 5,308,350 | A | 5/1994 | Mikhail | |
| 5,334,194 | A | 8/1994 | Mikhail | |
| 5,380,331 | A | 1/1995 | Mikhail | |
| 5,397,330 | A | 3/1995 | Mikhail | |
| 5,964,697 | A | 10/1999 | Fowler | |
| 5,964,698 | A | 10/1999 | Fowler, Jr. | |
| 6,117,072 | A | 9/2000 | Fowler, Jr. | |
| 6,409,731 | B1 | * 6/2002 | Masson et al. | 606/86 |
| 2002/0022211 | A1 | * 2/2002 | Horiguchi | 433/140 |

OTHER PUBLICATIONS

"Retractor Hooks attache to elastic coupler", Surgical Products, Oct. 1999, p. 1.
"Surgical Retractor Hooks", Orthopedic Technology Review, Jan. 2000, and Apr. 2000.
"The Lone Star Retractor System", Journal of Hand Surgery, Jan. 2000.
"The Lone Star Retractor System", Outpatient Surgery Magazine, Jan. 200, Feb., 2000, and Apr. 2000.
"Retract with Ease", Outpatient Surgery Magazine, May 2000.
"The Lone Star Retractor System", Foot & Ankle, Jan. 2000 and Feb. 2000.

* cited by examiner

*Primary Examiner*—Eduardo C. Robert
(74) *Attorney, Agent, or Firm*—Browning Bushman P.C.

(57) ABSTRACT

A ligament retractor assembly including a first retractor paddle, a second retractor paddle, a first elastic member having one end received in an opening of the first retractor paddle and an opposite end received by an opening of the second retractor paddle, and a second elastic member received in another opening of the first retractor paddle and an opposite end received in another opening of the second retractor paddle. Each of the first and second retractor paddles includes a first retaining section, a second retaining section and a lever section. The first and second retractor paddles are integrally formed of a polymeric material. The openings formed on the retaining sections of the paddles and each have a generally dog leg configuration.

12 Claims, 4 Drawing Sheets

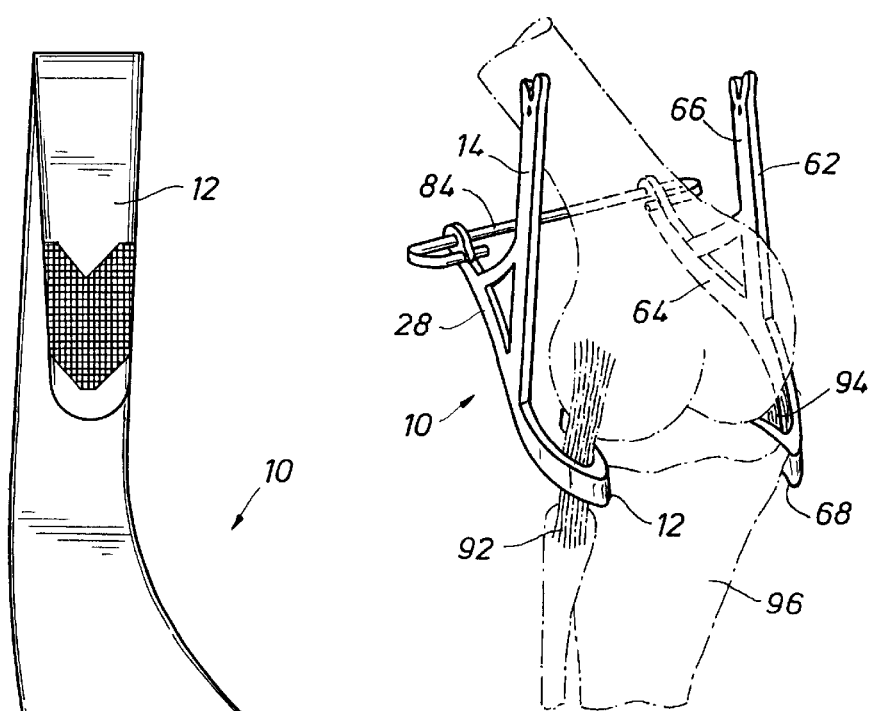
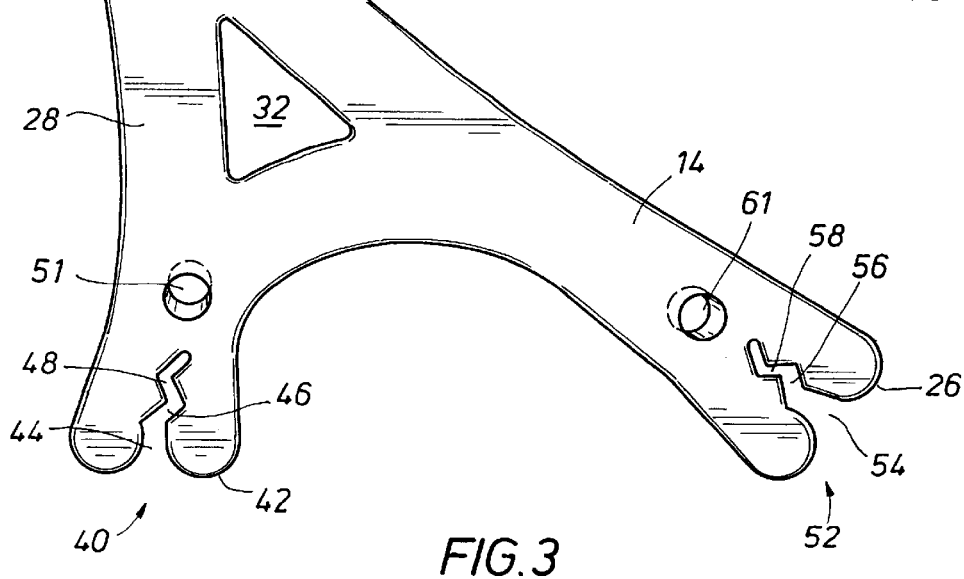
FIG.6
FIG.3

//

LIGAMENT RETRACTOR ASSEMBLY

RELATED U.S. APPLICATIONS

The present application is a continuation-in-part of U.S. patent application Ser. No. 10/109,099, filed on Mar. 29, 2002, and entitled "LIGAMENT RETRACTOR ASSEMBLY FOR USE IN PERFORMING KNEE SURGERY", presently pending.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to relates to retractor assemblies as used during surgical procedures. More particularly, the present invention relates to ligament retractors that are used during knee surgery.

BACKGROUND OF THE INVENTION

In performing knee surgery, it is of the utmost importance to avoid or to at least minimize damage to ligaments, tendons, muscles, nerves and other portions of the soft tissue while gaining access to and performing surgical procedures on various portions of the bone structure of the knee. Heretofore, retractors have been utilized in performing knee surgery so as to maximize access to the bone structure intended for osteotomy procedures while, at the same time, providing maximum protection for various soft tissue members. During the knee surgery, an appropriate incision is made along the forward area of the knee joint with the skin and flesh being parted to provide access to the joint. The flesh and the collateral ligaments are typically pulled or retracted laterally to expose the joints and held in this position by a hand held instrument, often referred to as a retractor. These hand-held retractors are held either by the surgeon or his assistant to maintain exposure to the joint to permit surgery to be performed.

In the past, various patents have issued relating to such collateral ligament retractors. For example, U.S. Pat. No. 4,520,797, issued on Jun. 4, 1985 to T. D. Petersen, discloses a collateral ligament retractor for use in knee surgery. This retractor includes a member having a cupped arcuate finger for insertion into the knee joint along and partly around the tibial plateau and a curved portion extending from the finger outwardly along the ligament, then extending back substantially in the same direction as the finger and including a downwardly extending pivoted elongated arm extending to a position behind the knee above the calf. A second member of similar design, but larger to accommodate the everted patella, is positioned around the opposite ligament. A tension member, such as a coil spring, is connected to the outer end of the arms of the members for biasing them toward one another to hold the ligaments in a retracted position.

U.S. Pat. No. 5,334,194, issued on Aug. 2, 1994 to W. W. Mikhail, teaches a collateral ligament retractor for use in performing knee surgery which includes a handle having a flat portion, an integral support section extending from the flat portion of the handle and following a curved path downwardly, and a tip extending from the integral support section and following a curved path in a reverse direction from that of the integral support section. The tip terminates in an end angled upwardly toward and below the plane defined by the horizontally positioned flat portion. The tip has edges tapering toward each other as they approach the end. U.S. Pat. No. 5,397,330, to the same inventor, describes a variation on the ligament retractor of U.S. Pat. No. 5,334,194. U.S. Pat. No. 5,397,330 is particularly utilized in association with posterior crticiate ligament surgery. U.S. Pat. No. 5,380,331, issued onto the same inventor on Jan. 10, 1995, describes alateral patellar retractor for use in performing knee surgery which has a similar structure in which the support and the prongs are sized to permit the prongs to engage the shelf of the lateral tibial condyle while the support is engaging soft tissue. U.S. Pat. No. 5,308,350, issued to the same inventor on May 3, 1994, shows a femoral distractor for use in knee surgery which includes a rod for insertion in the medullary canal of the femur and a detachable handle assembly. The detachable handle assembly permits the leg of a patient to be moved between positions of extension and flexion without the necessity of removing the rod from the medullary canal.

One of the major problems with these prior art ligament retractors is the fact that they are formed of a rigid steel material and utilize complicated spring-type mechanisms. As such, after each surgery, all of the items involved with the retractor assembly must be sterilized by autoclaving. As a result, the instruments are relatively expensive items. Since they are not disposable, additional costs are associated with the maintenance of such equipment. In other circumstances, since the instruments must be sterilized, they may, on occasion, be unavailable during surgery. Since each of the items described in these prior art patents are relatively expensive items, it is unlikely that the hospital will keep a large supply of such retractors available.

In other circumstances, the spring-type mechanism associated with these retractor assemblies may be inadequate in providing the proper tension to the surfaces being retracted. Since pre-tensioned coil springs are used by the prior art, they may not exert the proper tension required. Furthermore, during the surgical procedures, these prior art retractors do not provide a technique whereby the surgeon can increase the amount oftension applied to the collateral ligament retraction or to decrease the amount of tension. Also, because of the relatively complex nature of these retractor assemblies, the surgeon will require a great deal of time to be completely familiar with the proper operation of such items.

U.S. application Ser. No. 10/109,099, filed on Mar. 29, 2002, by the present inventors, describes one type of ligament retractor assembly including a first retractor paddle, a second retractor paddle and an elastic member having one end received in an opening of the first retractor paddle and an opposite end received by an opening of the second retractor paddle. Each of the retractor paddles includes a retaining section and a lever section. The lever section extends at a generally acute angle with respect to the retaining section. The first and second retractor paddles are integrally formed of a polymeric material. Each of these retractor paddles includes a gripping portion formed at an end of the retaining section adjacent the lever section. An opening is formed on the retaining section of the paddles so as to have a generally dog leg configuration opening at a side of the retaining section and extending at an angle toward a median of the retaining section. A hole is formed through the retaining section adjacent the opening.

It is an object of the present invention to provide a ligament retractor assembly which is disposable.

It is another object of the present invention to provide a ligament retractor assembly which can assure proper and adjustable tensioning, in an easy manner, during the course of the surgical procedure.

It is another object of the present invention to provide a ligament retractor assembly which does not require sterilization or autoclaving subsequent to surgery.

It is a further object of the present invention to provide a collateral ligament retractor assembly which is easy to use, relatively inexpensive, and easy to manufacture.

It is still another object of the present invention to provide a ligament retractor assembly which avoids contact with the popliteal vessels on the back of the knee.

It is a further object of the present invention to provide a ligament retractor assembly which is adaptable for being fixed around either the upper leg or around the calf.

It is still a further object of the present invention to provide a ligament retractor assembly which avoids a windshield wiper-effect caused by rotation relative to the knee.

These and other objects and advantages of the present invention will become apparent from a reading of the attached specification and appended claims.

BRIEF SUMMARY OF THE INVENTION

The present invention is a ligament retractor assembly comprising a first retractor paddle and a second retractor paddle, each having a lever section and first and second retaining sections. A first elastic member has one end received by the opening of the first retaining section of the first retractor paddle and an opposite end received by the opening of the first retaining section of the second retractor paddle. A second elastic member has one end received by the opening of the second retaining section of the first retractor paddle and an opposite end received by an opening in the second retaining section of the second retractor paddle.

In the preferred embodiment of the present invention, each of the first and second retractor paddles is a mirror image of each other. Each of the first and second retractor paddles is formed entirely of a polymeric material. Each of the first and second elastic members is a length of surgical tubing.

In the present invention, the second retaining section of each of the first and second retractor paddles branches outwardly from the respective retaining section of the first retractor paddle. The first retaining section is generally aligned with the lever section of the respective retractor paddle.

The opening in the first retaining section of each of the retractor paddles comprises an entry slot opening at an end of the first retaining section opposite the lever section, an inward slot communicating with an end of the entry slot opposite the end of the first retaining section and a retaining slot communicating with an end of the inward slot opposite the entry slot. Similarly, the opening of the second retaining section of each of the retractor paddles comprises an entry slot opening at an end of the second retaining section, an inward slot communicating with an end of the entry slot opposite the end of the second retaining section, and a retaining slot communicating with an end of the inward slot opposite the entry slot and angling toward the first retaining section.

In the present invention, the lever section has a concave surface extending therealong. This lever section includes scalloping extending along this concave surface.

Each of the first retractor paddles has a hole formed through the first retaining section adjacent to the opening of the first retaining section. The second retaining section of each of the retractor paddles also has a hole formed through the second retaining section adjacent to the opening of the second retaining section. The first elastic member extends through the hole in the first retaining section. The second elastic member extends through the hole in the second retaining section.

In the present invention, each of the first and second retractor paddles has a generally checkmark-shaped cross-section.

BRIEF DESCRIPTION OF THE SEVERAL VIEWS OF THE DRAWINGS

FIG. 3 is a side elevational view of the first retractor paddle of the present invention.

FIG. 6 is a perspective view showing the application of the ligament retractor assembly of the present invention as used during knee surgery.

DETAILED DESCRIPTION OF THE INVENTION

Figure 1:
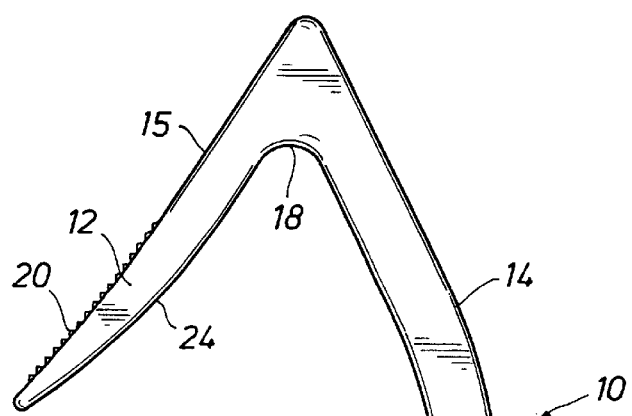
FIG. 1 is a side elevational view of the first retractor paddle of the present invention.

Referring to FIG. 1, there is shown the first ligament retractor paddle 10 in accordance with the teachings of the present invention. The ligament retractor paddle 10 includes a lever section 12 and a retaining section 14. The lever section 12 and the retaining section 14 are integrally formed together of a rigid polymeric material. The lever section 12 extends at an acute angle relative to the retaining section 14.

Since the retractor paddle 10 is formed of a polymeric material, the retractor paddle 10 can be easily disposed of subsequent to surgery. By injection molding the retractor paddle 10 in accordance with proper procedures, a large number of such retractor paddles can be formed at a relatively inexpensive cost. Suitable polymeric materials will provide the proper strength and rigidity to the structure of the retractor paddle so that it is properly functional during knee surgery.

As can be seen in FIG. 1, the lever section 12 has a slightly curved outer surface 15 extending from the juncture 18 with a retaining section 14. This slightly curved surface 15 of the lever section 12 will be suitable for fitting against the contour of the curvature of the tibia. As can be seen in FIG. 1, a scalloping 20 will extend along this outer surface 15 of lever section 12. The scalloping 20 provides a strong grasping surface on the outer surface 15. The opposite curved surface 24 of the lever section 12 can be smooth.

The lever section 14 extends at an acute angle with respect to the lever section 12. As will be described hereinafter, an opening will be formed at the end 26 of the retaining section 14 so that an elastic member can be received therein for retaining the lever section 12 in a properly tensioned relationship against the tibia for the purposes of retracting the ligament associated therewith.

Figure 2:
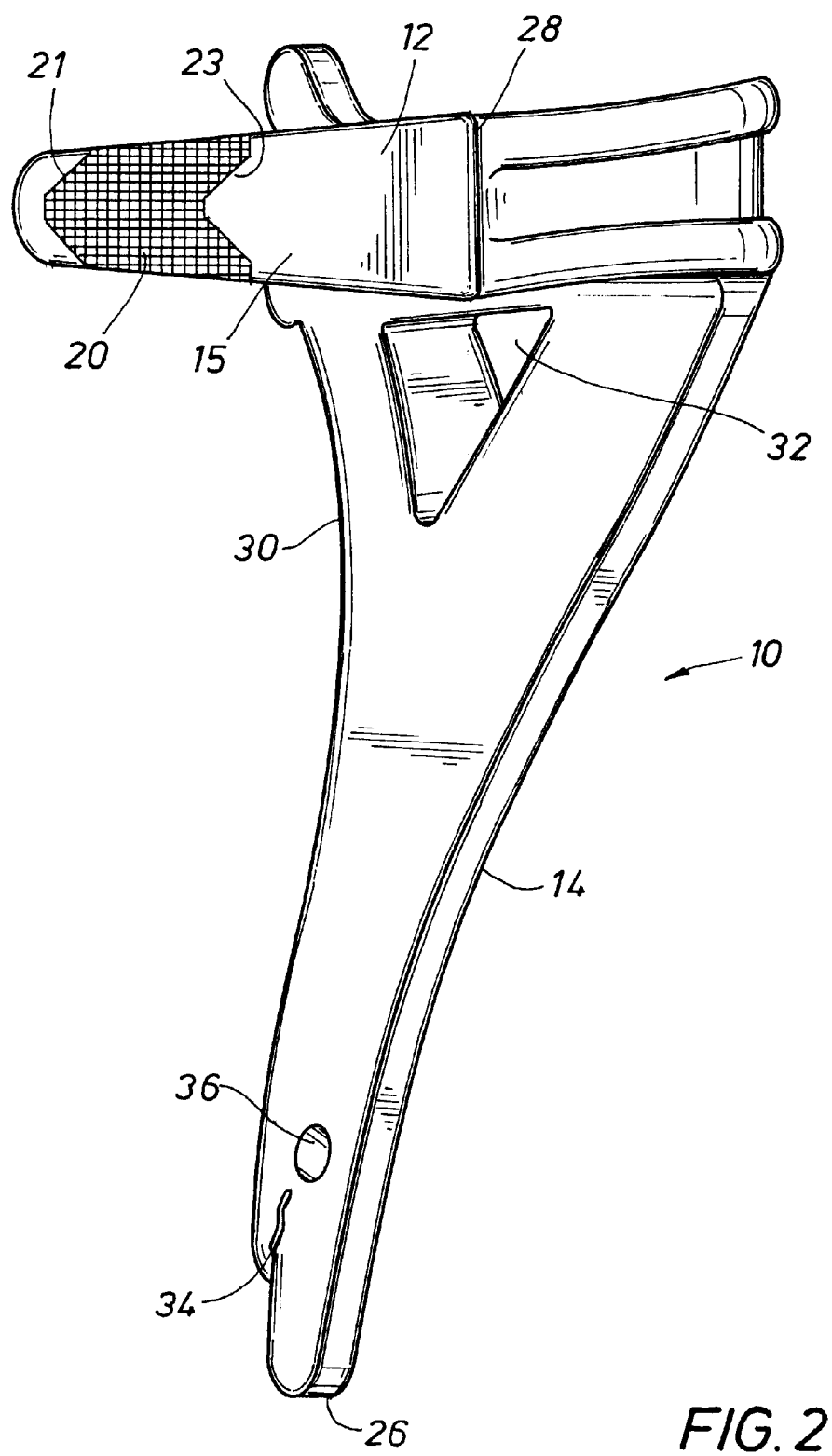
FIG. 2 is an upper perspective view of the first retractor paddle of the present invention.

FIG. 2 shows a perspective view of the retractor paddle 10. In particular, in FIG. 2, it can be seen that the lever section 12 is shown with its slightly curved outer surface 15. The curved surface 15, along with the scalloping 20, facilitates the ability to properly engage the bone structure. It can be seen that the scalloping 20 has a generally arrowhead shape with a V-shaped forward surface 21 and a V-shaped end surface 23. The scalloping 20 will extend generally transverse to the outer surface 15 of the lever section 12 between the ends 21 and 23.

FIG. 2 shows, with particularity, a first retaining section 28 and the second retaining section 14. It can be seen that the first retaining section 28 extends generally aligned with the lever section 12. The second retaining section 14 will extend outwardly, at an acute angle, with respect to the longitudinal axis of the lever section 12. A strut 30 connects the second retaining section 14 to the first retaining section 28. A hole 32 is formed in the structure of the retractor paddle 10 for the purpose of minimizing the amount of material required for the construction of the retractor paddle 10 and also for the purposes of facilitating the ability to injection mold the retractor paddle 10.

FIG. 2 also shows the opening 34 formed at the end 26 of the second retaining section 14. A hole 36 is formed inwardly from the opening 34.

FIG. 3 shows the configuration of the lever section 12, the first retaining section 28 and the second retaining section 14. Opening 32 is illustrated as being of a triangular configuration formed between the first retaining section 28 and the second retaining section 14. An opening 40 is formed at the end of the first retaining section 28 opposite the lever section 12. Opening 40 has a generally "dog leg" configuration so as to open along the end 42 of the second retaining section 28 and to extend generally toward the lever section 12. The opening 40 includes an entry slot 44 which has one end opening along the end 42 of the retaining section 28. Entry slot 44 extends inwardly from the end 42. An inward slot 46 communicates with an end of the entry slot 44 opposite the end 42 and extends further toward the lever section 12 for a small distance. A retaining section 48 has one end communicating with an end of the inward slot 46 opposite the entry slot 44 and extends further toward the lever section 12. The retaining section 48 is particularly configured so as to receive the compressed surgical tubing inserted into opening 40 during the surgical procedure. It is important to note that the "dog-leg" structure of the opening 40 assures a secure fixing of the surgical tubing within the slot. This provides a measure of safety so as to prevent accidental release of the surgical tubing from its position within the opening 40 during the surgical procedure. Experiments with the present invention have shown that the circuitous route of the opening 40 will prevent any accidental release of the surgical tubing retained therein. Hole 51 is formed through the retaining section 28 adjacent to the opening 40. The surgical tubing can be threaded through the hole 51 so as to have an end extending outwardly therefrom. This end can then be inserted through the various slots 44, 46 and 48 associated with opening 40.

Similarly, it can be seen that the second retaining section 14 has an opening 42 formed at the end 28 of the second retaining section 14. Opening 52 will have a configuration similar to that of opening 40 including, in particular, an entry slot 54, an inward slot 56 and a retaining slot 58. Opening 52 can be configured so as to extend longitudinally along the second retaining section 14 in a direction toward the first retaining section 28. A hole 61 is formed through the retaining section 14 adjacent to the opening 52. The surgical tubing will be threaded through the hole 61 so as to have an end extending outwardly therefrom. This end can then be inserted through the various slots 54, 56, and 58 associated with opening 52.

Figures 4, 5:
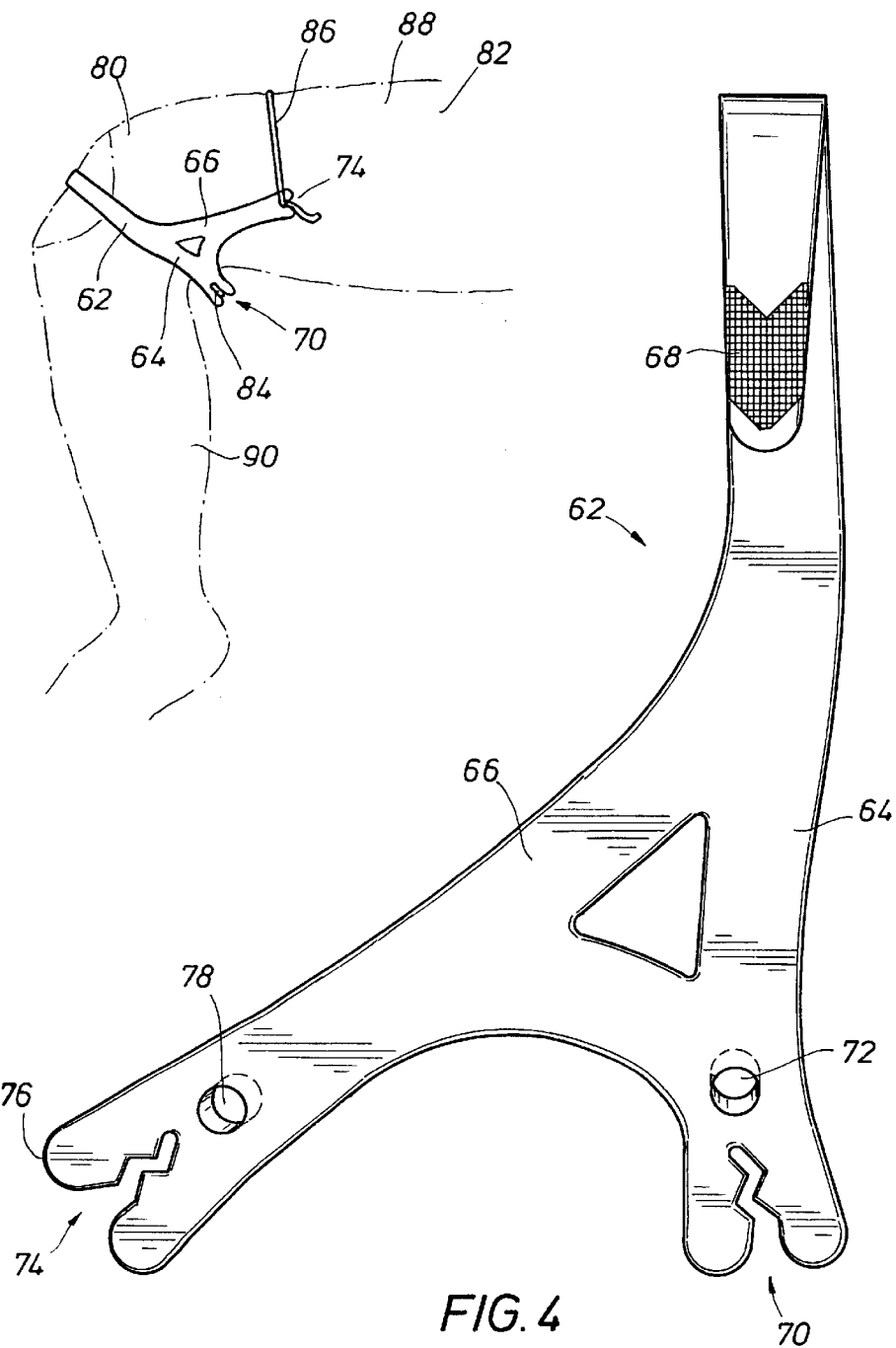
FIG. 4 is a side elevational view of the second retractor paddle of the present invention.
FIG. 5 is a diagrammatic illustration of the application of the first and second retractor paddles onto the knee of a patient during knee surgery.

FIG. 4 shows a side elevational view of a second retractor paddle 62 associated with the ligament retractor assembly of the present invention. The second retractor paddle 62 is a mirror image of the first retractor paddle 10. It includes a first retaining section 64 and a second retaining section 66. A lever section 68 extends at an acute angle with respect to the first retaining section 64. The first retaining section 64 has an opening 70 formed at an end thereof opposite the lever section 68. Opening 70 has a similar dogleg-shaped configuration as openings 40 and 52 associated with the first retractor paddle 10. A hole 72 is formed adjacent to the inwardmost end of the opening 70. The second retaining section 66 also has an opening 74 formed at an end opposite the lever section 68. Opening 74 extends inwardly from the end 76 of the second retaining section 66 in a direction toward the first retaining section 64. A hole 78 is formed adjacent to the innermost end of the opening 74.

Both retractor paddles 10 and 62 are employed during the surgical procedure. A first length of the surgical tubing is utilized so as to have one end extending through hole 41 and received within opening 40 associated with the first retractor paddle 10 and an opposite end extending through hole 72 and received within opening 70 of the second retractor paddle 62. Generally, a second length of surgical tubing will have one end extending through hole 61 and received within opening 52 of the second retaining section 14 of the first retractor paddle 10 and an opposite end extending through hole 78 and received within opening 74 of the second retaining section 66 of the second retractor paddle 62. By providing proper tension to the surgical tubing, the proper tensioned relationship of the lever sections 12 and 68 associated with the retractor paddles 10 and 62, is achieved. In the preferred embodiment of the present invention, the retractor paddles 10 and 62 are mirror images of one another. As a result, the length of the surgical tubing received in holes 51 and 72 will extend rearwardly behind the knee of the patient. Holes 61 and 78 will have a length of surgical tubing extending therebetween over the lower thigh portion above the knee of the patient. Alternatively, if the mirror imaged retractor paddles 10 and 62 are reversed, the length of elastic tubing extending through holes 61 and 78 can be positioned around the upper calf below the knee of the patient. As such, the present invention can be suitably manipulated depending upon the physical size and shape of the knee region of the patient.

FIG. 5 shows the application of the retractor paddles 10 and 62 around the knee 80 of the patient 82. In particular, it can be seen that the second retractor paddle 62 is secured around one side of the knee 80 of patient 82. The first retaining section 64 extends outwardly beyond the back of the knee 80. A first length of elastic tubing 84 is received in the opening 70. The elastic tubing 84 will extend in spaced relationship behind the knee 80 of the patient 82. The second retaining section 66 extends upwardly from the first retaining section 62 toward the upper region of the knee 80. A second length of the elastic tubing 86 is received within the opening 74. Elastic tubing 86 will extend over the top of the lower portion of the thigh 88 of the patient 82. The first retractor paddle 10 will have an identical configuration on the opposite side of the knee 80. Importantly, the placement of the second elastic tubing 86 will prevent any windshield wipering-effect from occurring from any tension placed upon the retractor paddles 10 and 62 during bending of knee

80. Additionally, the elastic tubing 84 will be suitable spaced from the back to knee 80 so as to avoid direct contact with the popliteal vessels on the back of the knee.

Importantly, the retractor paddles 10 and 62 can be suitable reversed so that the elastic band 86 will be placed around the upper calf 90 of the patient 82. In such a configuration, the first retractor paddle 10 is used in the location of the second retractor paddle 62 and the second retractor paddle 62 is used in the location of the first retractor paddle 10. The use of the dual points of connection between the elastic bands 84 and 86 and the respective retractor paddles 10 and 62 will effectively prevent rotation of the respective retractor paddles during the surgical procedure This configuration will provide a greater degree of adaptability to the flexibility of the knee 80 of the patient. The present retractor paddles are self-retaining during the surgical procedure.

FIG. 6 shows the retaining section 28 of the first retractor paddle 10 as extending outwardly from the lever section 12. Similarly, the retaining section 64 of the second retractor paddle 62 extends outwardly from the lever section 68 thereof. The retractor paddles 10 and 62 each have a generally checkmark-shaped cross-section including the slightly curved concave lever sections 12 and 68 which are adapted to extend along and to curve around the tibia to a pivot point. The lever sections 12 and 68 are suitably concave so as to extend around both in a horizontal and a vertical direction for fitting around the tibial plateau. The retaining section 28 extends outwardly from the lever section 12. The surgical tubing 84 is illustrated as extending through the holes formed in the respective retaining sections 28 and 64 of the retractor paddles 10 and 62. The end of the surgical tubing is looped backwardly through the respective retaining sections so that one end of the surgical tubing 84 is received within the opening 40 of the retaining section 28. Similarly, the tubing 84 will have an end received by a corresponding opening associated with the retaining section 64 of the retractor paddle 62.

Figure 7:
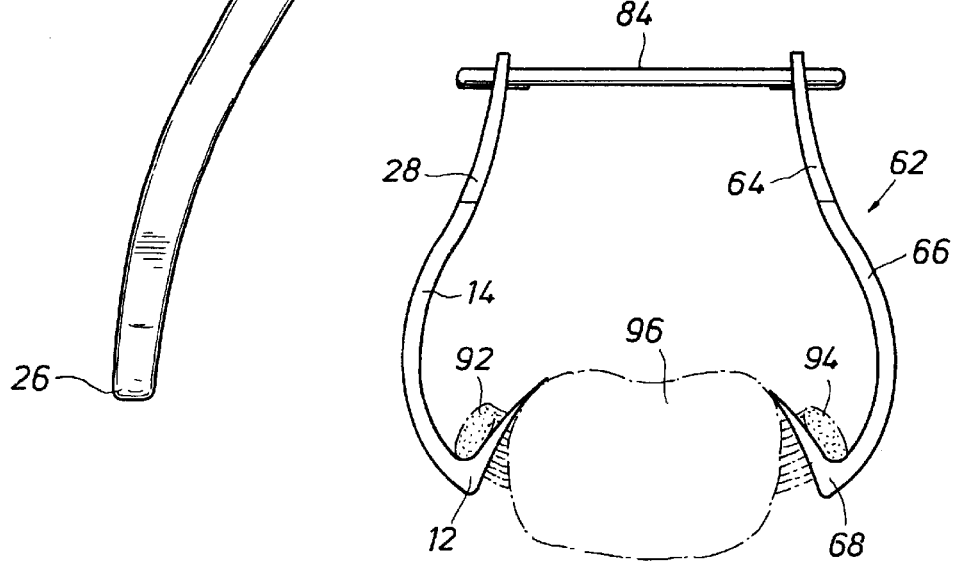
FIG. 7 is an interior view showing the application of the ligament retractor assembly during knee surgery.

It will be appreciated that, in viewing FIGS. 6 and 7, that the space between the lever member 12 and the retaining member 28 is filled with a collateral ligament 92 and that the space between the lever 68 and the retaining section 64 is filled with a collateral ligament 94. Additionally, flesh, everted patella and bandages, or the like, can also be included in such spaces. The above-described material is pulled away from the front of the knee joint and held in a retracted position, as illustrated, by the retractor paddles in the position shown in FIGS. 6 and 7. The tubing 84 is particularly illustrated in tension so that the collateral ligaments 92 and 94 are separate from the bone structure 96. The combination of the retractor paddles 10 and 62, along with the surgical tubing 84, functions as levers to retract the ligaments 92 and 94. These ligaments 92 and 94 are held in position by the tension of the surgical tubing 84 without the aid of the surgeon or assistant. As a result, it will free the hands of the surgeon and his or her assistant for the operation. The pivoted retaining sections 28 and 64 of the respective retractor paddles 10 and 62 enable the lever members 12 and 68, respectively, to be positioned so that the knee can be flexed without interfering with the retractor assembly. These pivoting members allow self-adjustment and permanent flexing and extending of the leg or joint as needed. When it is necessary to apply additional retracting force to the collateral ligaments 72 and 74 during surgery, the surgical assistant can simply grasp the respective retaining sections 28 and 64 or the retaining sections 14 and 66, and pull. Following that procedure, the surgical assistant can then release these retaining sections. The elastic tubing and the configuration of the retractor paddles 10 and 62 assures that the retractor paddles 10 and 62 will return to their original position.

The retractor assembly of the present invention provides an effective hands-off retractor that frees the hands of the surgeon for the operation. It can be appreciated that the retractor paddles can be utilized individually and can be hand held. The unique shape and curvature thereof provides a simple and effective retractor that is easily and conveniently utilized for different sizes of knee structure. The retractor assembly of the present invention is somewhat universal and can be used on substantially any size of knee. The retractor assembly of the present invention is of a size having sufficient structural strength and dimensions to perform its function while, at the same time, is small enough to be utilized without interfering with the surgical procedure.

Since the retractor assembly of the present invention utilizes polymeric retractor paddles 10 and 62, along with lengths of surgical tubing 84 and 86, the retractor paddles 10 and 62 and the surgical tubing 84 and 86 can be simply disposed after use. The present invention avoids the need for autoclaving and sterilization subsequent to surgery. There will always be availability of the retractor assembly of the present invention since large numbers of such retractor assemblies can be easily manufactured and provided at a relatively low cost.

In actual practice, surgeons are often familiar with the tension afforded by surgical tubing. As such, the surgeon will have a better "feel" of the tension applied by the surgical tubing 84 and 86 during the surgical procedure. If greater tension is required, the surgeon can simply adjust the tension in the surgical tubing 84 and 86 by pulling the surgical tubing from the opening and applying greater tension. If less tension is required, then the surgeon can pull the surgical tubing from the opening and release some of the tension. The amount of tension applied by the surgical tubing 54 is virtually infinitely variable. As such, the surgeon will be given a greater "feel" of the retractor assembly during the surgical procedure.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

We claim:

1. A ligament retractor assembly comprising:
    a first retractor paddle having a lever section and a first retaining section and a second retaining section, said lever section extending from said first and second retaining sections, each of said first and second retaining sections having an opening therein;
    a second retractor paddle having a lever section and a first retaining section and a second retaining section, said lever section of said second retractor paddle extending from said first and second retaining sections of said second retractor paddle, said each of first and second retaining sections of said second retractor paddle having an opening therein;
    a first member having one end received by said opening of said first retaining section of said first retractor paddle and an opposite end received by said opening of said first retaining section of said second retractor paddle; and a second member having one end received by said opening of said second retaining section of said first retractor paddle and an opposite end received by said opening of said second retaining section of said second retractor paddle.

2. The assembly of claim 1, each of said first and second retractor paddles being a mirror image of each other.

3. The assembly of claim 1, each of said first and second retractor paddles being formed of a polymeric material.

4. The assembly of claim 1, each of said first and second members being a length of surgical tubing.

5. The assembly of claim 1, said second retaining section of said first retractor paddle branching outwardly from said first retaining section of said first reactor paddle.

6. The assembly of claim 5, said first retaining section of said first retractor paddle being generally aligned with said lever section of said first retractor paddle.

7. The assembly of claim 1, said opening of said first retaining section of said first retractor paddle comprising:

an entry slot opening at an end of said first retaining section of said first retractor paddle opposite said lever section and extending inwardly toward said lever section of said first retractor paddle;

an inward slot communicating with an end of said entry slot opposite said end of said first retaining section and extending therefrom at an angle toward said lever section of said first retractor paddle; and a retaining slot communicating with an end of said inward slot opposite said entry slot, said retaining slot angling back from said inward slot toward said lever section said first retractor paddle.

8. The assembly of claim 7, said opening of said second retaining section of said first retractor paddle comprising:

an entry slot opening at an end of said second retaining section of said first retractor paddle;

an inward slot communicating with an end of said entry slot opposite said end of said second retaining section and extending therefrom for a distance toward a side of said second retaining section of said first retractor paddle; and a retaining section communicating with an end of said inward slot opposite said entry slot, said retaining section angling back toward said first retaining section.

9. The assembly of claim 1, said lever section of said first retractor paddle having a concave surface extending therealong.

10. The assembly of claim 9, said lever section having scalloping extending across at least a portion of said concave surface.

11. The assembly of claim 1, said first retractor paddle having a hole formed through said first retaining section of said first retractor paddle adjacent said opening of said first retaining section of said first retractor paddle, said second retaining section of said first retractor paddle having a hole formed through said second retaining section of said first retractor paddle adjacent said opening of said second retaining section of said second retractor paddle, said first elastic member extending through said hole of said first retaining section of said first retractor paddle, said second elastic member extending through said hole of said second retaining section of said first retractor paddle.

12. The assembly of claim 1, each of said first and second retractor paddles having a generally checkmark-shaped cross-section.

* * * * *